United States Patent [19]

Herrmann et al.

[11] Patent Number: 5,805,051
[45] Date of Patent: *Sep. 8, 1998

[54] INTERACTIVE MEDICATION REMINDER/DISPENSER DEVICE

[75] Inventors: James M. Herrmann; Gerald S. Indorf, both of Amherst, N.H.; Sunway R. Wang, Andover, Mass.

[73] Assignee: IntelliMed, Inc., Amherst, N.H.

[ * ] Notice: This patent issued on a continued prosecution application filed under 37 CFR 1.53(d), and is subject to the twenty year patent term provisions of 35 U.S.C. 154(a)(2).

[21] Appl. No.: 725,830

[22] Filed: Oct. 7, 1996

[51] Int. Cl.$^6$ .................................................. G08B 1/00
[52] U.S. Cl. .................. 340/309.4; 340/309.15; 364/569; 368/10; 221/2
[58] Field of Search .................. 368/10; 221/2, 221/3, 15; 364/569; 340/309.4, 309.5, 309.15

[56] References Cited

U.S. PATENT DOCUMENTS

| | | | |
|---|---|---|---|
| 4,616,316 | 10/1986 | Hampeter et al. | 364/413 |
| 4,626,105 | 12/1986 | Miller | 368/10 |
| 4,682,299 | 7/1987 | McIntosh et al. | 340/309.4 |
| 4,725,997 | 2/1988 | Urquhart et al. | 221/15 |
| 4,911,327 | 3/1990 | Shepherd et al. | 221/3 |
| 4,939,705 | 7/1990 | Hamilton et al. | 221/2 |
| 4,971,221 | 11/1990 | Urquhart et al. | 221/2 |
| 5,016,172 | 5/1991 | Dessertine | 128/630 |
| 5,072,430 | 12/1991 | Eckernas et al. | 221/3 |
| 5,170,380 | 12/1992 | Howard et al. | 221/2 |
| 5,181,189 | 1/1993 | Hafner | 221/2 |
| 5,200,891 | 4/1993 | Kehr et al. | 364/413.01 |
| 5,239,491 | 8/1993 | Mucciacciaro | 221/15 |
| 5,246,136 | 9/1993 | Loidl | 221/2 |
| 5,392,952 | 2/1995 | Bowden | 221/15 |

*Primary Examiner*—Michael Horabik
*Assistant Examiner*—Timothy Edwards, Jr.
*Attorney, Agent, or Firm*—Jacob N. Erlich; Jerry Cohen

[57] ABSTRACT

An interactive, automated medication reminder/dispenser device having a housing and a container operably associated with the housing for containing and dispensing therefrom at least one predetermined type of medication. An audio and visual output for provides a visual and audio signal indicative of a time to take at least one medication and additional medication located external of the container, and further indicative of a dosage of medication to take at a preselected time. The device also includes a recording system for providing an indication of each of the medications which have been taken, the recording system being activated by the application of a signal thereto. This activation signal is responsive to either the opening of the container or an independent action. In addition, the device can preselectively vary input in order to vary the time and dosage, with a signal being provided of the varied time and varied dosage which can vary from once a day to numerous times a day for each of the medications and the varied dosages can vary for each of the varied time and for each of the medications.

22 Claims, 12 Drawing Sheets

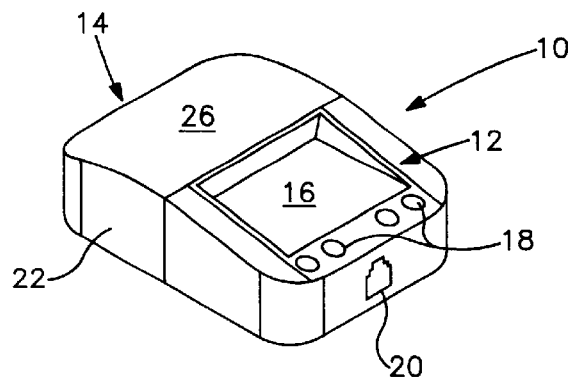
FIG. 1
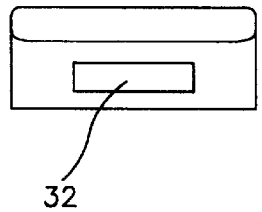
FIG. 2
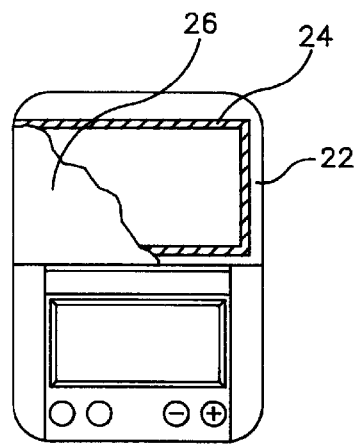
FIG. 3
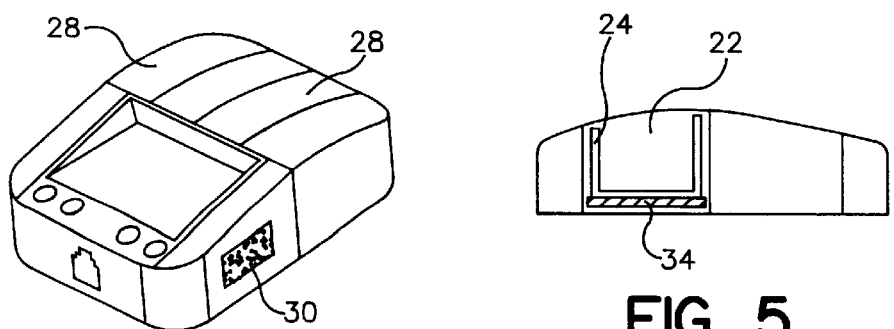
FIG. 4
FIG. 5

| Interval | Description | Default Time | Advance Hrs | Skip Hrs |
|---|---|---|---|---|
| qd | each day | 8:00 | 6 | 12 |
| bid | twice each day, constant or variable dosage | 8:00  20:00 | 3 | 6 |
| tid | three times each day, constant or variable dosage | 7:00  14:00  22:00 | 1.75 | 3.5 |
| qid | four times each day, constant or variable dosage | 6:00  12:00  17:00  12:00 | 1.25 | 2.5 |
| hs | at bed time | 22:00 | 4 | 4 |
| ac | before meal | 7:00  12:00  18:00 | 1.25 | 2.5 |
| pc | after meal | 7:00  12:00  18:00 | 1.25 | 2.5 |
| qod | each other day | 8:00 | 12 | 20 |
| CYCL | each day, cycle dosage | 8:00 | 6 | 12 |
| GRAD | each day, gradual change dosage | 8:00 | 6 | 12 |

FIG. 17

INTERACTIVE MEDICATION REMINDER/DISPENSER DEVICE

FIELD OF THE INVENTION

This invention relates generally to medication dispensers and, more particularly, to a pocket-sized, portable, microprocessor-controlled device capable of providing medication and/or information to a user representative of a wide range of medication related parameters.

BACKGROUND OF THE INVENTION

It is well recognized that the self-taking of prescribed and nonprescribed medications by individuals, especially the elderly, has drastically increased over the years. This is especially true in instances when medication can be taken in the home to combat diseases which, in the past required hospitalization. Unfortunately, the adverse effect to a patient who has either improperly taken the correct dosage of medication or who has failed to take medication at all has, in many instances, counteracted the benefits of derived from the proper administration of this medication. With the decrease in the amount of time patients are required to be hospitalized, the self-administration of medication without proper supervision has drastically increased.

There are a number of devices in use today which provide some form of visual and/or audible indication of medication to be taken. However, there is still a substantial need in the marketplace for an extremely compact device, which is easy to use, and which has a series of redundant safety features incorporated therewith to enable a patient or individual to self-administer the taking of prescribed medications in preselected dosages and at preselected times. In addition, it would be especially useful to provide such a device with the interactive capability of being programmed by physicians and pharmacists as well as having the capability for easy patient input. Furthermore it would also be desirable if the device could provide interactive capability as well as being able to receive information from an external source.

It is therefore an object of this invention to provide an extremely small, preferably pocket-sized portable electronic device that reminds the user of time and dosage information for a wide variety of dosing timing patterns.

It is another object of this invention to provide a device which can handle dosing intervals ranging from alternate daily reminders to multiple reminders per day, and with the capability of providing variable dosage information each time including, for example half-tablet and liquid dispensing information.

It is still a further object of this invention to provide a device which is capable of both visually and audibly providing dispensing information on an easily-read display screen, a gentle chime, physical motion of a part or all of the device, e.g. vibration, or by oral pre-programmed messages for utilization by both the visually and hearing impaired.

It is an even further object of this invention to provide a device which has the interactive capability of being pre-programmed by physicians, pharmacists or users themselves, either by inputting information by way of keys, voice commands, plug-in modules or directly from an external computer source or through telephone lines.

It is an even further object of this invention to provide a device which is capable of providing accurate information with respect to the amount of medication taken, and in which redundant inputs can be correlated as a safety feature.

It is still a further object of this invention to provide a device which can include sealed medication units capable of only being installed within the device by an authorized source and programmed in accordance with coded information on the prescription vial.

It is an even further object of this invention to provide a device which includes a scanning mechanism capable of accepting coded information from prescription vials for automatically programming the device.

It is an even further object of this invention to provide a device which incorporates therein a supplemental or back-up power source which will retain current prescription information until the main power source has been replaced.

SUMMARY OF THE INVENTION

The present invention overcomes problems associated with past devices utilized for the dispensing of medication. More specifically, the medication reminder/dispenser or device of the present invention is a lightweight, pocket-sized portable electronic aid configured preferably in a "mouse-like" configuration having an easily readable display and audible source for providing a wide variety of prescription and other related parameters to assist a user of self-dispensed medication. The device also includes a container unit capable of receiving a plurality of different medications either in the form of tablets or capsules. In addition, the container unit can be either filled by the user or other individual such as a pharmacist or physician or can be adapted to receive a prescription vial which is inserted within the device of this invention by a pharmacist. Medication therefrom may be released to the user by a program provided by the pharmacist or physician. A further embodiment of the invention could incorporate therein a "voice-chip" capable of orally providing pre-programmed information to a patient with respect to medication dosage and time of usage to those who may be visually impaired to such a degree that the accurate reading of the display screen may be impossible.

A cover encloses the medication container unit so as to prevent contamination thereof. The cover can be opened manually by the pressing of a button when the appropriate time for medication has occurred or it can be opened by the activation of an electronic or mechanical release based on a signal received from the on board electronics. A redundant, interactive system may also be included with the present invention in which the user inputs information by way of a key representative that he or she has taken the medication at the appropriate time. This information may be compared with a signal received from a switch activated by the opening of the cover. A further embodiment of the present invention could include an extremely sensitive pre-programmed weighing mechanism such as, for example, a strain gauge mechanism, or the like, which can imbedded within the base of the medication container units so as to ascertain the removal of tablets or caplets based on weight. As an alternative, an optical or mechanical system may be utilized to determine when medication has been removed from the device. This information is then analyzed to accurately ascertain the actual taking of the medication.

Examples of typical information displayed or output from the reminder/dispenser device of the present invention includes information with respect to the time and date the medication is to be taken. This information can be varied to accommodate variable dosages or staggered time intervals. In addition, visual or oral messages may indicate gradual change of dosages over time and indications whether the medication should be taken before or after meals or at bedtime. Factual information can also be presented, for example, should the medication be taken with food or without food and other related warnings which would normally be placed upon the prescription bottle. Further information can be provided by the reminder/dispenser device of this invention with respect to medication located external of the device as well as liquid dosages.

Examples of the type of information which could be recorded within the device includes information with respect to the last medication time, the next medication time, the medication interval and specified time for taking the medication (all of which can be varied over time), dosage, and total pills left within the dispenser.

For a better understanding of the present invention, together with other and further objects, reference is made to the following description taken in conjunction with the accompanying drawings, and its scope will be pointed out in the appended claims.

BRIEF DESCRIPTION OF THE DRAWINGS

FIG. 1 is a pictorial representation of the interactive medication reminder/dispenser device of this invention;

FIG. 2 is a rear view of the interactive medication reminder/dispenser device of FIG. 1 illustrating the position of a container unit cover release button;

FIG. 3 is a plan view of the interactive medication reminder/dispenser device of this invention illustrating the location of the medication container unit located within the body of the device;

FIG. 4 is a pictorial representation of an alternate embodiment of the interactive medication reminder/dispenser device of this invention in which a plurality of container units in which each of the units has a separate, openable cover associated therewith;

FIG. 5 is a side elevational view illustrating the medication container in conjunction with a sensitive weight-measuring device for ascertaining the number of tablets or capsules contained therein;

FIG. 17 is a chart showing examples of the various interval default settings provided by the device of the present invention.

DETAILED DESCRIPTION OF THE PREFERRED EMBODIMENTS

Figure 6:
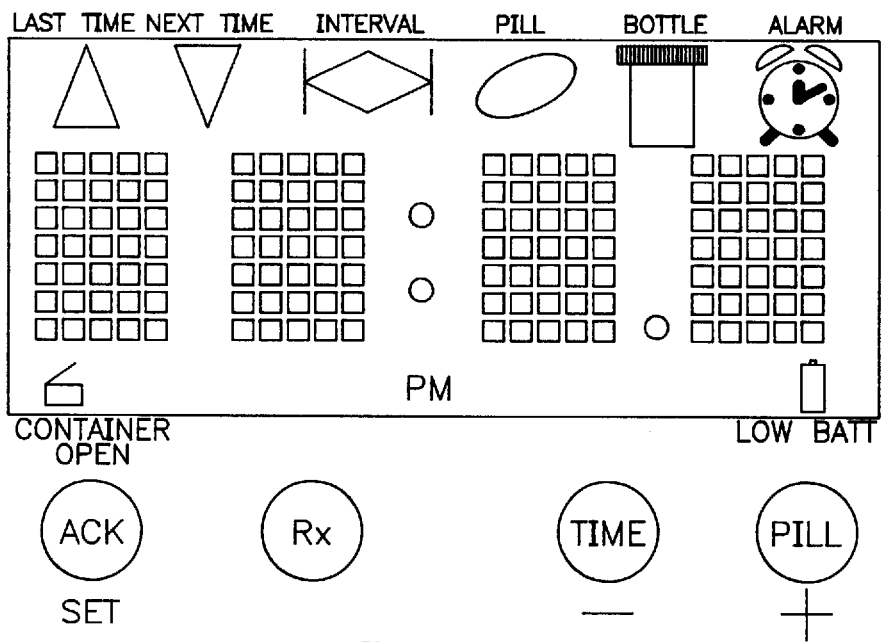
FIGS. 6 and 7 are illustrations of typical display units utilized with present invention.

Reference is now made to FIG. 1 of the drawings which pictorially represents the interactive medication reminder/dispenser device 10 of this invention. As illustrated in FIG. 1, the device 10 is configured in a easily held and attractive "mouse-like" configuration having a front portion 12 and a rear portion 14. The front portion 12 contains a display 16 with programmable keys 18 (the exact number of keys may vary within the scope of this invention) located adjacent thereto. Although the display 16 and keys 18 are shown in FIG. 1 in a specific location on the reminder/dispenser device 10 of this invention, it should be realized that their position can be altered with respect to one another and still remain within the confines of this invention.

Also, located on the front portion of reminder/dispenser device 10 is a phone jack receptacle 20 utilized to provide access to input data in a matter to be described in greater detail hereinbelow. It should also be realized that receptacle 20 can be located in different positions around the body of device 10. At the rear portion of the device is a housing 22 which is clearly depicted in FIGS. 3 and 5 of the drawings having a container unit 24 and a cover 26 as shown in FIG. 1 or a plurality of covers 28 for a plurality of container units as shown in FIG. 4. The container unit 24 may be in the form of a disposable covered tray made of any suitable FDA approved ABS plastic, the material used in manufacturing standard prescription vials. Furthermore, the container unit 24 may be replaced by sealed prescription vials which operate in conjunction with a release mechanism (not shown). The sealed vials can be inserted in the housing 22 by a pharmacist or doctor. In the embodiment of the invention utilizing sealed vials, input data for the use of the medication contained therein may be programmed into the device 10 by the pharmacist or doctor. Additionally, the container may be in the form of A separate unit (not shown) used in conjunction with the other components of device 10. In such a case, the other components of the device 10 would be in a separate unit as well which would be sized to fit or be placed on top of the separate container.

A further embodiment of this invention may include a scanning unit 30 which can be formed integral with the body of reminder/dispenser device 10 as shown in FIG. 4 of the drawings or connected external therefrom (not shown). By passing a coded prescription vial in front of the scanning unit 30, the on-board computer within the reminder/dispenser device 10 can read in appropriate information with respect to the dosage and time that medication is to be taken by a patient.

FIG. 2 of the drawings illustrate the rear of the reminder/dispenser device 10 and contains a button 32 which is activated by the user in order to release a latch on cover 26 and permit the cover 26 to open for access to the container unit 24. Either the opening of cover 26 or covers 28 or the pressing of release button 32 sends a signal to the onboard computer of reminder/dispenser device 10 of this invention indicating the cover has been opened. This information can, therefore, be part of the programmed information of the onboard computer to inform the user that medication has been taken at a predetermined time. It is possible to also control the utilization of the release button 32 so that it can only be pressed to open cover 26 or covers 28 within a predetermined time interval after an audible or visual signal has been produced by the device.

A further embodiment of the invention may include a sensitive weighing mechanism in the form of, for example, an extremely sensitive strain gauge 34 as illustrated in FIG. 5. The weighing mechanism would enable the device to compare weights based upon the removal of pills or capsules contained within the container unit 24. By so doing, it would be possible to accurately determine if a medication has actually been taken. This information is utilized by comparing this output with a signal provided by the pressing of cover release button 32 so as to verify the fact that the cover 26 or covers 28 have been opened and a pill or capsule has, in fact, been removed. If a discrepancy occurs between these signals, then an indication could be provided by the visual display screen indicating this discrepancy. The importance of accurately determining whether or not medication has been taken is especially useful with individuals who may be forgetful and open the cover 26 or covers 28 to take the prescribed medication, but in reality, forget to do so. Alternatively, optical or mechanical systems may also be incorporated in device 10 to determine when medication has actually been taken.

The reminder/dispenser device 10 of this invention can also be utilized with medication obtained from an external source. In such an instance an activation key which may be located on the front of reminder/dispenser device 10 can be pressed by the user upon taking the external medication which, for example, may be either in the form of pills, capsules or liquid.

Figure 7:
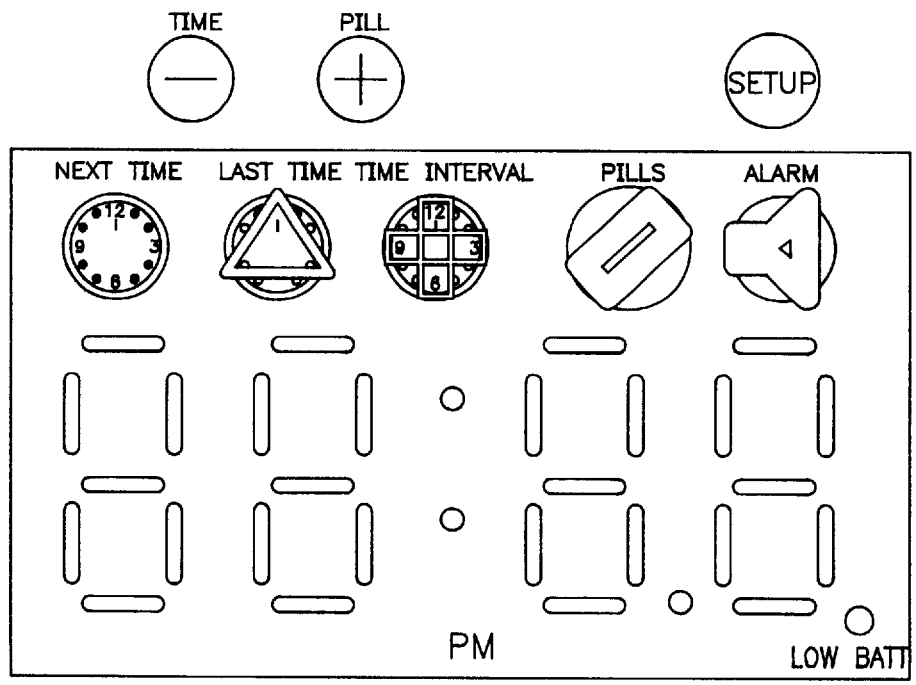

Typical examples of the LCD display and set-up keys used with this invention are illustrated in FIGS. 6 and 7 of the drawings, and their interrelationship with various input and output information is described hereinbelow. It should also be noted that in other embodiments of the invention the visual display 16 or 16' may work in conjunction with audible chimes, LCD flashes, artificial voice reminders or even vibration of the device so that the device can be used by the visual impaired. The artificial voice can be produced by a preprogrammed voice chip which provides voice output indicative of the information visually displayed. These multiple reminders reinforce the message that the medication should be taken and, furthermore, provides excellent redundancy with respect to the type of dosage and time of day or night this medication should be taken.

In general, the reminder/dispenser device 10 may be programmed very simply either by a pharmacist, doctor, or user and, in addition, has default programs for the entire range of prescription dose intervals. Any of these parameters may be changed in the set-up mode. Opening the cover 26 (28), for medication kept within the device, or pressing a specific key for medication usage timed by the device but stored external of the device resets the timer and records the time that the medication was taken. With respect to medication kept in the container units, additional means may be utilized in conjunction therewith to obtain an accurate count or indication whether the pills or capsules contained within the container have actually been taken. Such redundancy allows the user or doctor to recall when the medication was last taken. This is especially effective in those instances when a user is not sure whether or not an appropriate dose was taken.

Provided below is a description of the flow diagrams shown in FIGS. 8–16 of the drawings. It should be noted that in the following description of the flow diagrams identical buttons or keys may be given different reference numerals in order to aid in following the flow diagrams as the sequence of operations change.

Figure 8:
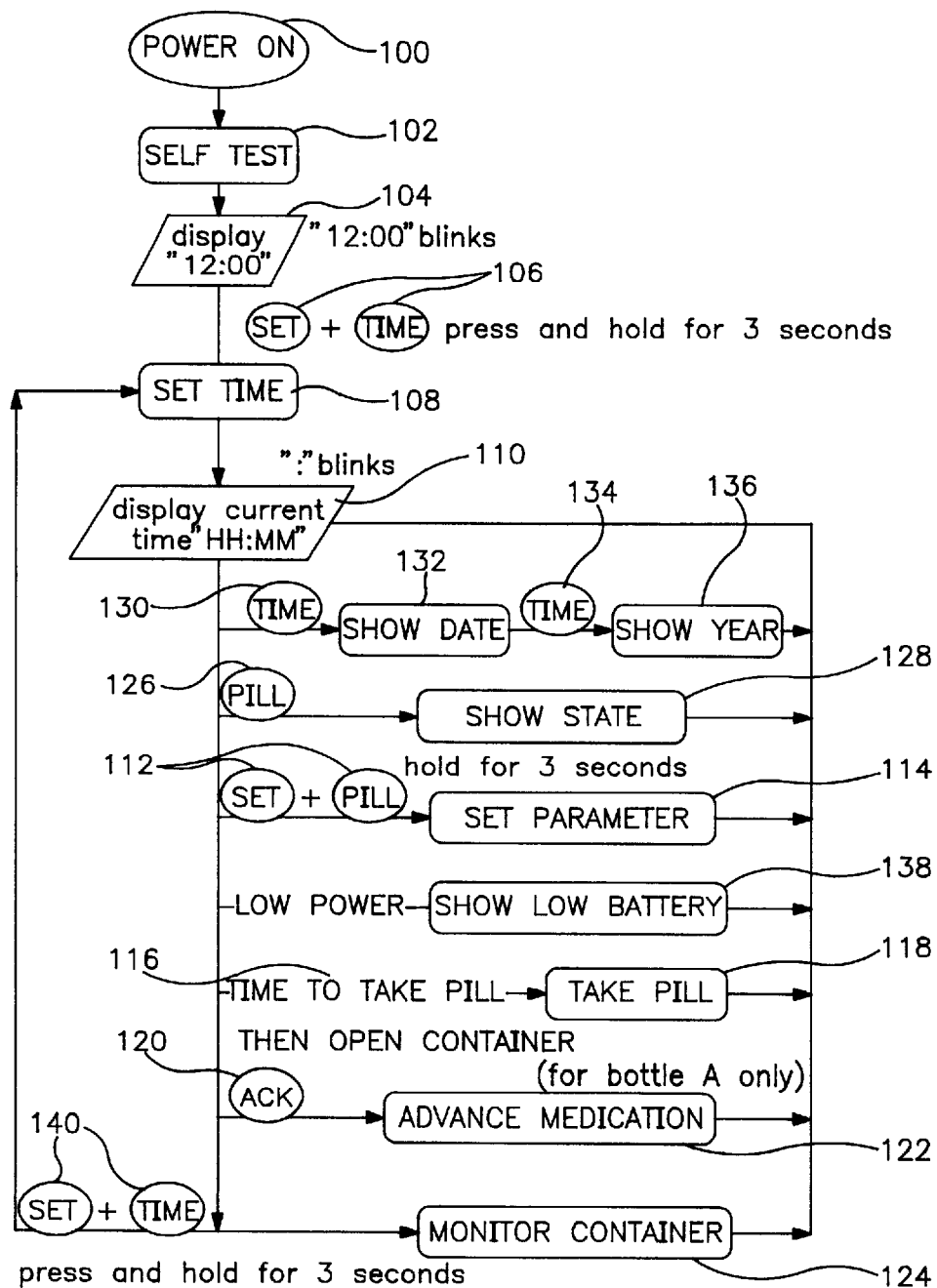
FIGS. 8–16 are flow diagrams illustrative of various programmable information contained within the interactive medication reminder/dispenser device of this invention.

FIG. 8 represents a main flow diagram that describes the "power on" sequence and all of the possible states that could occur with the inventive device 10. Device 10 is preferably battery operated with the device being in a "power save" mode when the system is inactive. When a battery is inserted, device 10 goes into a "self test" mode 102 where the memory, LCD display, container switch and speaker are initiated. The time display 104 blinks indicating that the time has not been programmed. Simultaneously depressing both the SET and TIME keys 106 for more than three seconds puts the device 10 into set time mode 108. The device 10 will enter a default mode 110 in which it will display the real time and the ":" will blink once a second.

Depressing both the SET and PILL keys 112 for more than 3 seconds allows the user to set parameters 114 indicative of when a particular pill should be taken. Later an indicator 116 will notify the user when that particular pill should be taken 118. If, within the preset time zone (as illustrated and described with reference to FIG. 17), the user holds the ACK key 120 when opening the container portion of device 10 earlier than the designated medication time, the device 10 will skip the alarm for that time. This action is called the ADVANCE MEDICATION mode 122. Further description of setting parameters are provided below with respect to FIGS. 13 and 14.

A positive monitoring system 124 within device 10 can sense when a pill has been removed from the container of device 10 or when the container has been improperly opened. By depressing the PILL key 126, the status 128 of device 10 will be shown on display 16; that is the number of pills or other medication remaining will be shown. By depressing the TIME key 130, the display 16 will show the current date 132. The display 16 will show current year 136 by depressing the TIME key 134 again. Also, there is a LOW BATTERY indicator 138 to remind the user to replace the battery. The real time clock can be changed by simultaneously depressing the SET and TIME keys 140 again.

Figure 9:
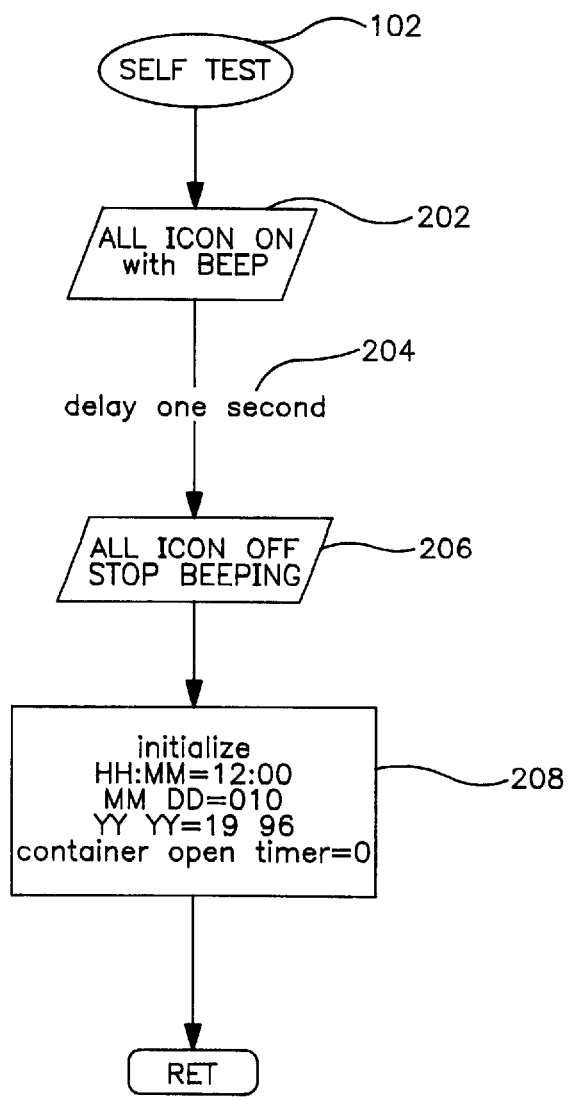

Reference is now made to FIG. 9 to describe the SELF TEST mode 102 sub-flow diagram that describes what will be tested and initialized after power-up. During the self test, all icons and LCDs are lit and a beep 202 sounds for one second 204 to check the display 16 and speaker. Thereafter, the light and sound 206 are turned off. This action 208 initializes the time clock, timers, and sets all pill numbers to zero.

Figure 10:
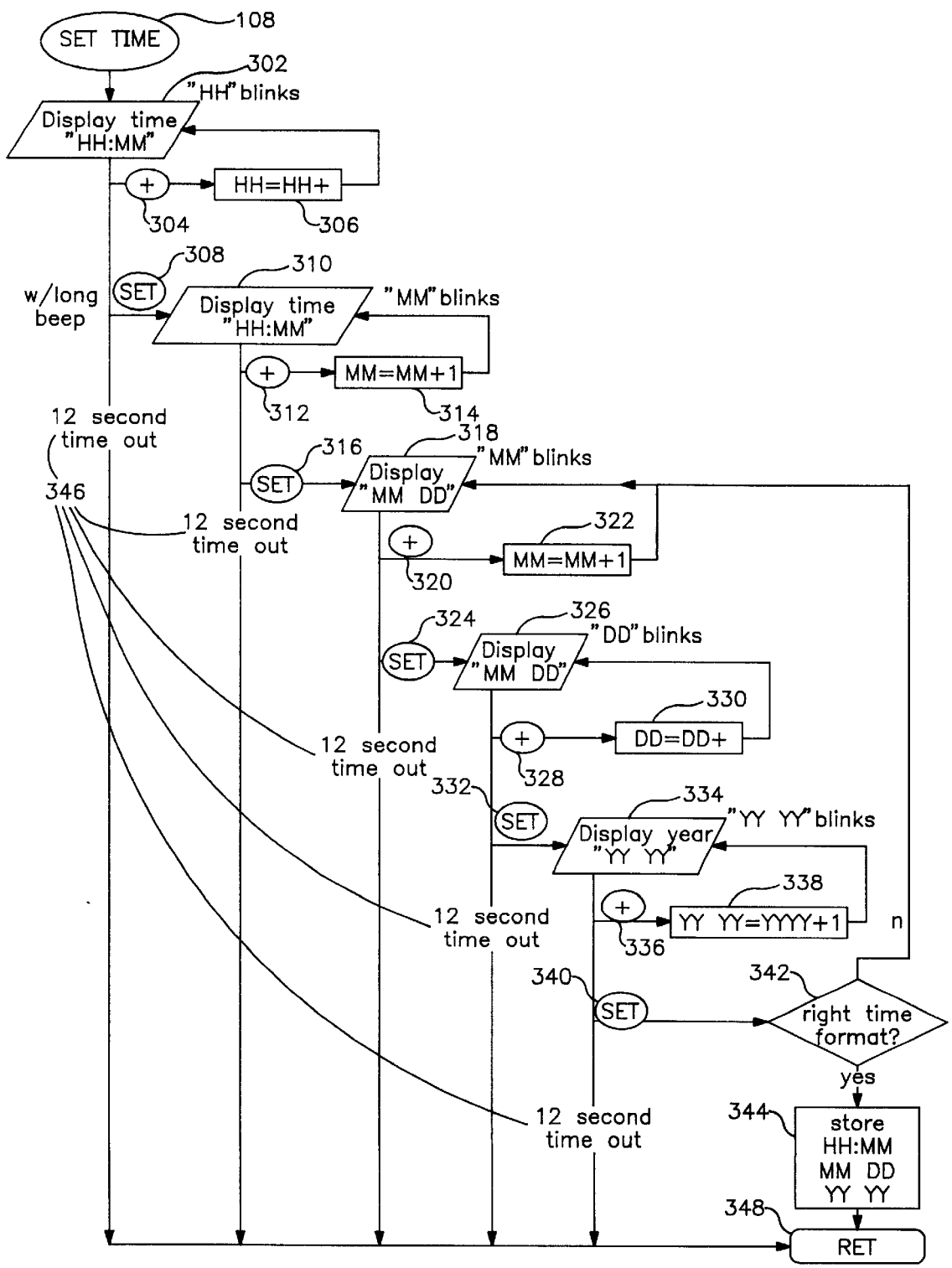

FIG. 10 illustrates the SET TIME mode 108 sub-flow chart in order to describe the procedure for setting the real time clock. Blinking of HH 302 indicates the time clock displayed can changed at this time. Depressing the "+" key 304 will increase the hour number 306. More specifically, holding the "+" key, will move the hour increment faster. By depressing the SET button 308 the device 10 will set minute mode 310. Thereafter depressing the "+" key 312 forwards the minute number 314, and holding the "+" key in will fast forward the minutes. Thus, the user can set the month, date and year (316, 318, 320, 322 324, 326, 328, 330, 332, 334, 336 and 338). When SET key 340 is pressed for the last time the program will perform a check to determine whether the year is a "leap year" before storing the real time 344 and entering the real time clock mode. The device 10 allows a predetermined number of seconds to pass (preferably 12 seconds) as indicated at 346 after which, if no key is depressed, the program will return to the real time clock mode 348.

Figure 11A:
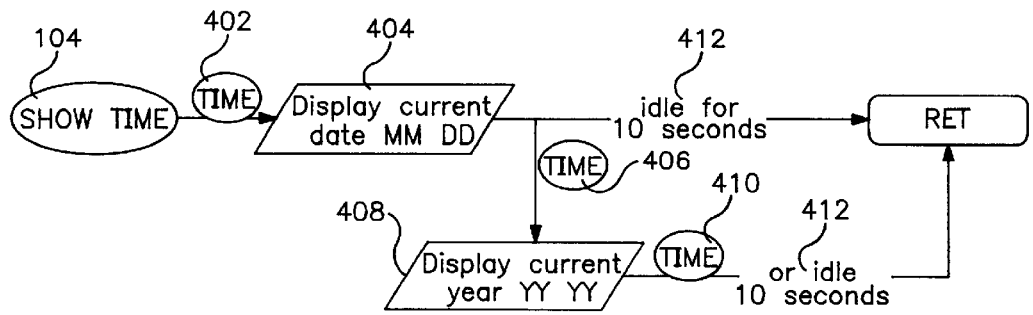
Figure 11B:
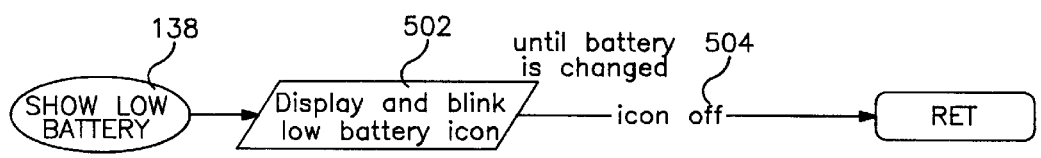
Figure 11C:
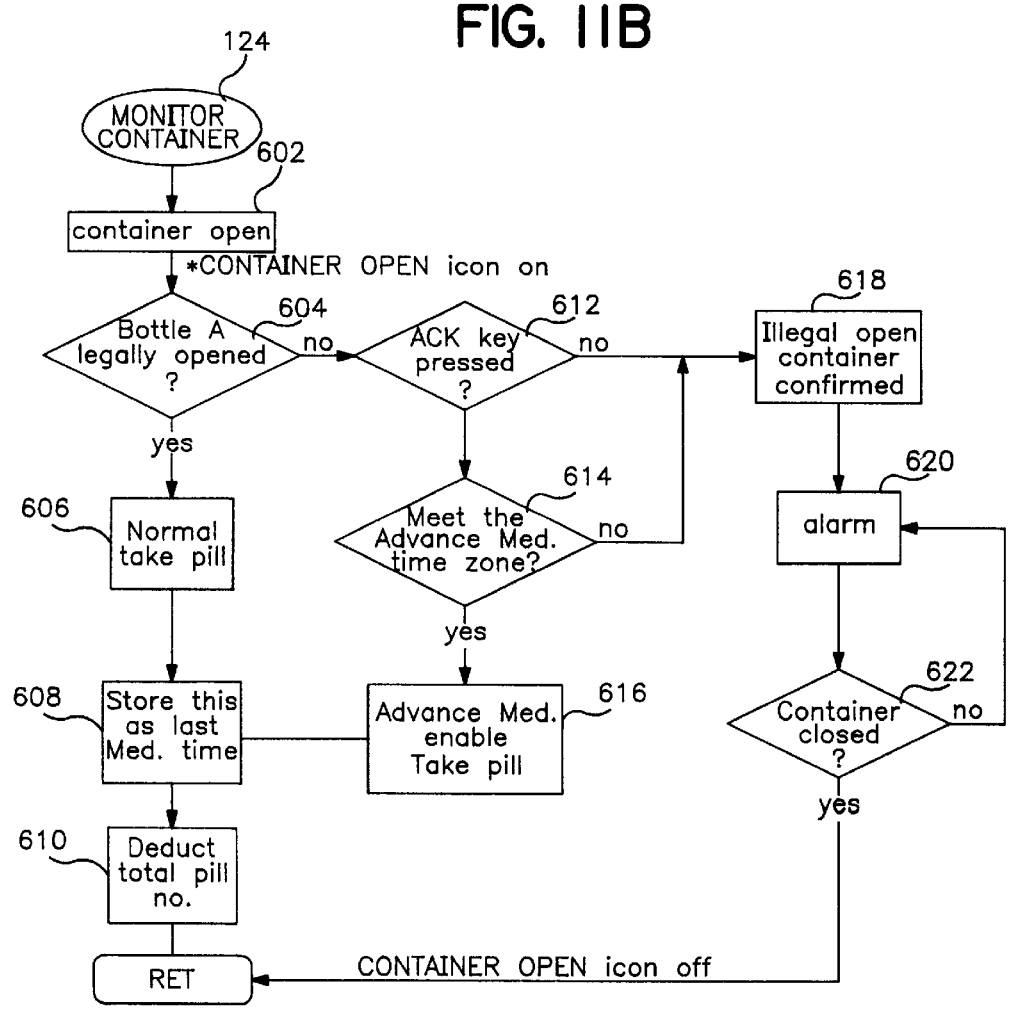

Three subroutine examples are illustrated in FIGS. 11A–11C (also referred to as FIG. 11). The SHOW TIME routine 104 shown in FIG. 11A displays the current month, day and year. By depressing the TIME button 402, the display 16 will show the current month and day 404. By depressing the TIME button 406 again, the display will show the current year 408. Depressing the TIME button 410 once more or merely permitting device 10 to be idle for a predetermined time (preferably the total 10 seconds) as indicated at 412 the device 10 will return to the default real time clock.

The SHOW LOW BATTERY routine 138 shown in FIG. 11B warns the user of a low battery power condition. When the low voltage sensor detects low power, the low power icon 502 blinks until the battery is replaced.

FIG. 11C shows the MONITOR CONTAINER routine 124 which detects if the container is opened at the right condition and time. When the container is opened as indicated at 602, the system monitors the conditions in order to ascertain if the opening is proper. If it is the appropriate time to take a pill 606, the time that the container was opened will be recorded as a pill is taken at that time 608. Also at this time, a pill will be deducted from the total number of pills as shown at 610.

If the container is opened at a time other than the normal pill taking time by depressing the ACK key 612, this will correspond to an advanced medication time zone 614, and this will be set as an advance medication condition noted at 616. If this advanced opening time does not meet the advance medication time zone 614 or the ACK key 612 is not pressed at all, or if the container opens at other than the normal taking pill time as indicated at 604, an alarm 620 will sound to warn the user of this unacceptable opening of the container as shown at 618. The alarm will sound until the container is closed as indicated at 622.

Figure 12:
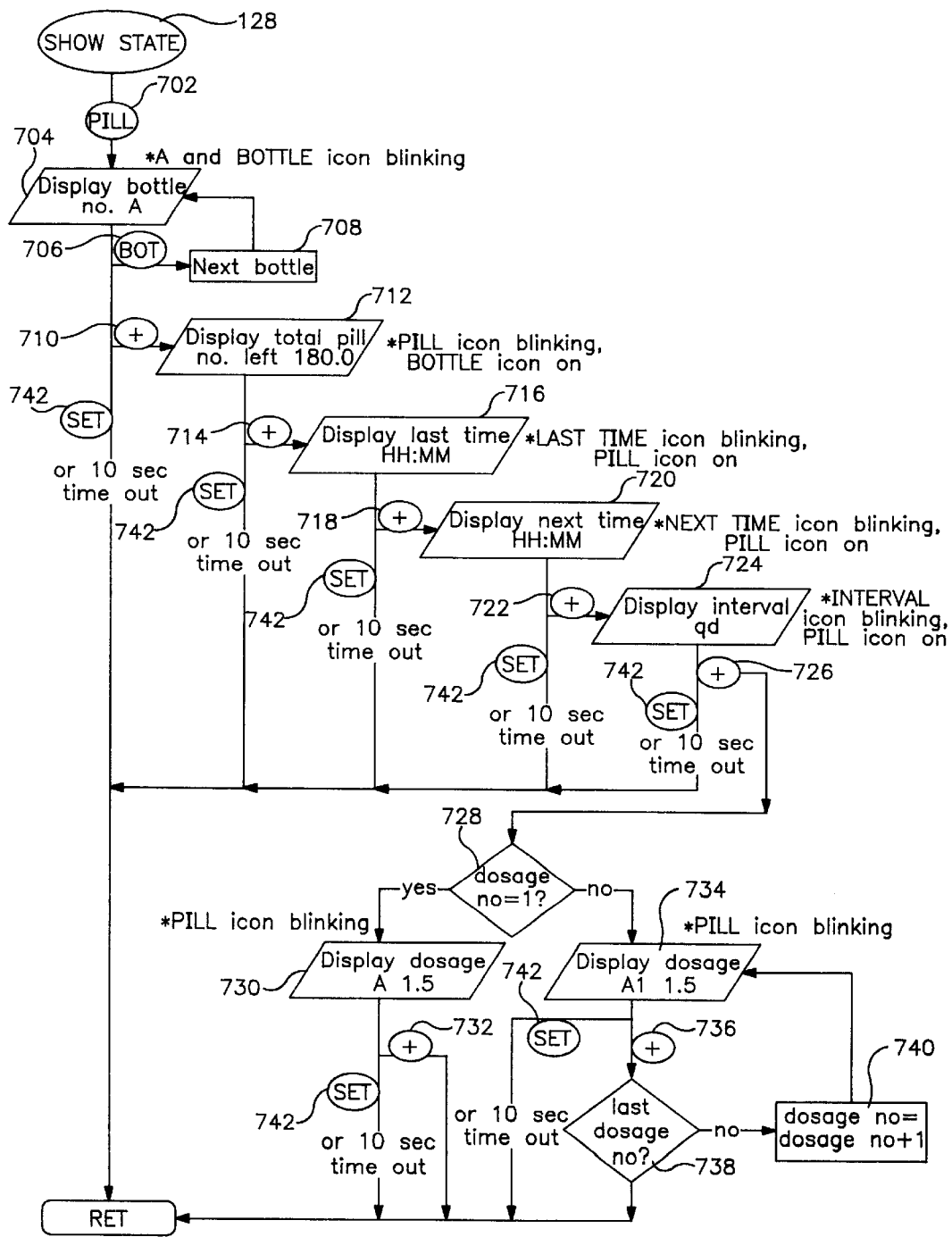

FIG. 12 illustrates the condition or state of the container and external bottles as SHOW STATE 128 is displayed. Depressing the PILL key 702 at the default real time clock state puts the device into the SHOW STATE mode 128.

The LCD then displays and blinks A (generally designating the container 24 within device 10) and bottle icon 704 to show that the following states are for bottle A (i. e. the container 24 within device 10). Depressing the BOT key 706 moves the display to B, C, D or E 708 (these bottles are normally external of device 10) in sequence for further bottles. By depressing the "+" key 710 at this time, the LCD will display the total number of pills left 712 in the displayed bottle. The PILL icon will blink and the BOTTLE icon will light. By depressing the "+" key 714 again, the LCD will display last time 716 a pill has been taken, the LAST TIME icon will blink and PILL icon will light. Depressing the "+" 718 again, the LCD will display next time 720 to take a pill, the NEXT TIME icon will blink and the PILL icon will light. Depressing the "+"722 once again, the LCD will display the interval 724 between taking pills, the INTERVAL icon will blink and the PILL icon will light. If it is a single dosage prescription 728, depressing the "+"726 will cause the LCD to display the bottle number and next time dosage 730 together with the PILL icon blinking. Then by pressing the "+" key 732 or SET key 742 the clock mode will return to real time. If the prescription dosage 728 is variable, depressing the "+" key 726 will cause the LCD display to show the bottle number and dosage and blink PILL icon 734. Sequentially depressing the "+" key 736 will sequentially show the dosage 740 until the last dosage 738 is shown. Depressing the SET key or doing nothing for 10 seconds will put the device back to default real time clock.

Figure 13:
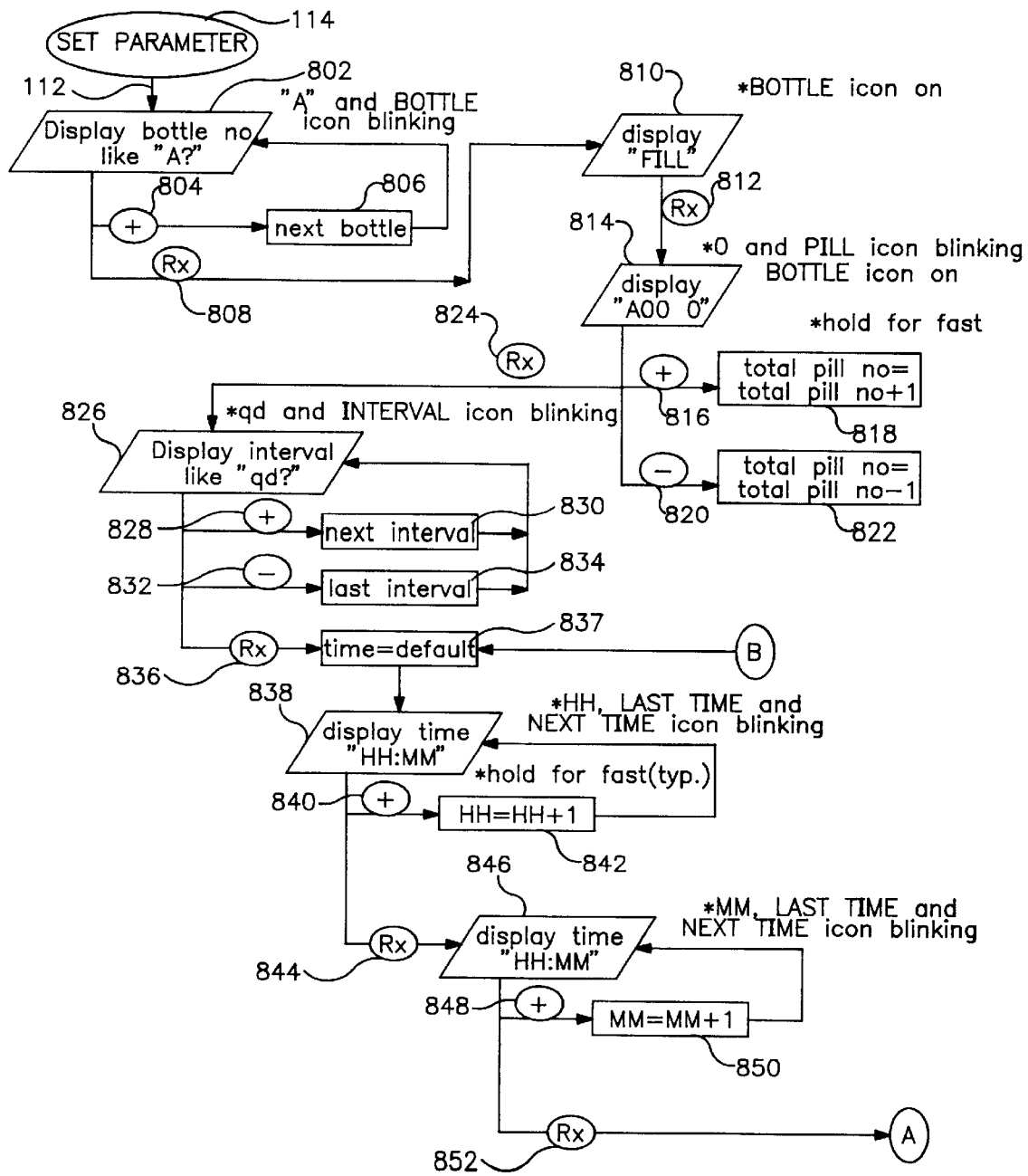
Figure 14:
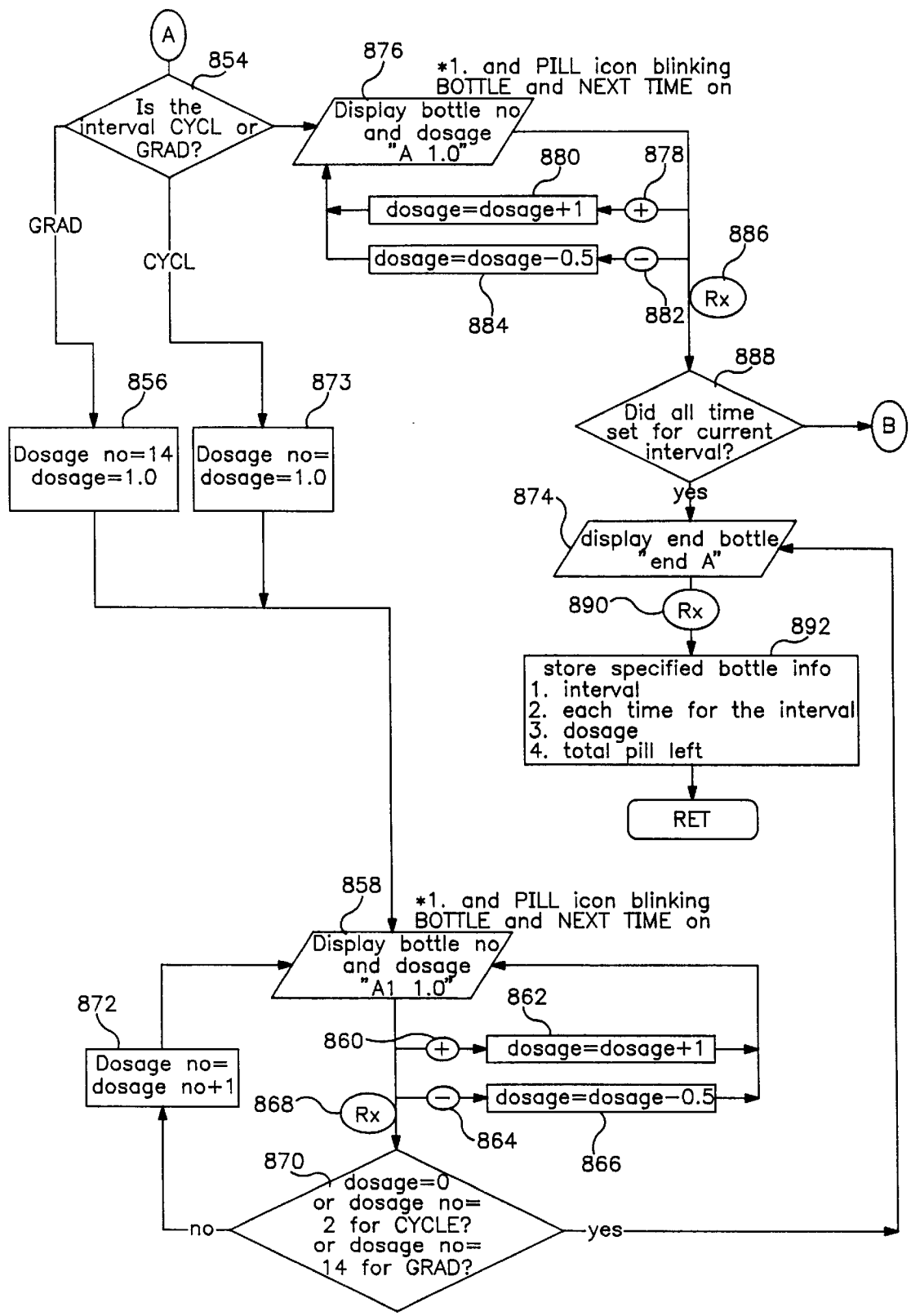

FIGS. 13 and 14 show the procedures of setting the parameters and timers. Holding the SET and PILL keys simultaneously for 3 seconds 112 puts the device into the SET PARAMETER mode 114. The LCD will display bottle A (container 24) and blink BOTTLE icon 802 first, then depressing the "+" key 804 will sequentially change the bottles (A, B, C, etc.) 806. Depressing Rx 808 enables the user to program the parameters for the bottle last displayed. Displaying FILL 810 enables the user to enter the total pill number first. The LCD will display the bottle designation and the total number 814 of pills with the PILL icon blinking and BOTTLE icon lit. Now depressing the "+" key 816 will increase the total pill number 818, while pressing the "−" key 820 will decrease the total pill number 822. Depressing the Rx key 824 again sets the medication interval. The LCD then shows the medication interval 826 with the INTERVAL icon blinking. The INTERVAL icon provides an indication of the interval period at which the medication is to be taken as, for example, shown in the chart of FIG. 17. This interval period is described as follows: "once each day" (qd); "twice daily" (bid); "three times each day" (tid); "four times each day" (qid); "at bed time" (hs); "before meals" (ac); "after meals" (pc); "every other day" (qod); "cyclic dosages each day" (CYCL); and "graduated dosages each day" (GRAD).

Each of the intervals has its own default time as shown in FIG. 17. However, these times can be changed in the manner set forth below.

As shown in FIG. 13, pressing the "+"828 will change to the next interval 830, while pressing the "−" key 832 will change to last interval 834. Pressing Rx key 836 again sets the medication time. The LCD then displays the medication time 838 with the HOUR, LAST TIME and NEXT TIME icons blinking to indicate that it is now time to set the hour the pill is to be taken. The medication time is initiated with default time.

Pressing the "+" key 840 increases the hour number 842, with holding the "+" key for fast forward. Pressing the Rx key 844 once again will enable the user to set the minute for taking the pill. When displaying the medication time 846 the MINUTE, LAST TIME and NEXT TIME icon are blinking. The user depresses the "+" key 848 to increase the minute number 850, holding the "+" key for fast forward. Depressing the Rx key 852 sets the dosages.

As shown in FIG. 14, if the interval is GRAD 854, the maximum dosage number is shown at 856 while displaying the bottle designation, with the DOSAGE NUMBER and the DOSAGE ICON 858 and PILL icon blinking and the BOTTLE and NEXT TIME icon lit. This permits the user to set the dosage by depressing the "+" key 860 to increase the dosage 862 by one at each press and by depressing the "−" key 864 to decrease the dosage 866 by 0.5. Depressing the Rx key 868 will set the next dosage 872 if the dosage number is not 14 or the dosage is not zero as shown at 870.

If the interval set at CYCL 854, the maximum dosage number shown at 873 is 2, displaying the bottle designation, dosage number and dosage, with the DOSAGE icon 858 and PILL icon blinking and the BOTTLE and NEXT TIME icons it. The user can depress the "+" key 860 to increase the dosage 862 by one at each press and depress the "−" key 864 to decrease the dosage 866 by 0.5. Depressing the Rx key 868 again sets the next dosage 872 if dosage number is not 2 or dosage is not zero. This parameter set is finished as shown at 873 if the dosage is zero or the dosage number is 2 shown at 870. At this time "end A" is displayed to show that the end of the bottle A setting is completed. Depressing the Rx key 890 two times exits the SET PARAMETER mode 114 and all the input data is saved 892.

If the interval is neither GRAD nor CYCL 854; when the bottle number and dosage 876 is displayed with the PILL icon blinking, and the BOTTLE and NEXT TIME icon is lit, depressing "+" 878 or "−" 882 in the same fashion as setting the dosage at the GRAD interval will set the dosage. Depress Rx 886 to end the setting 874 if all of the dosages are set 888 as desired.

Figure 15:
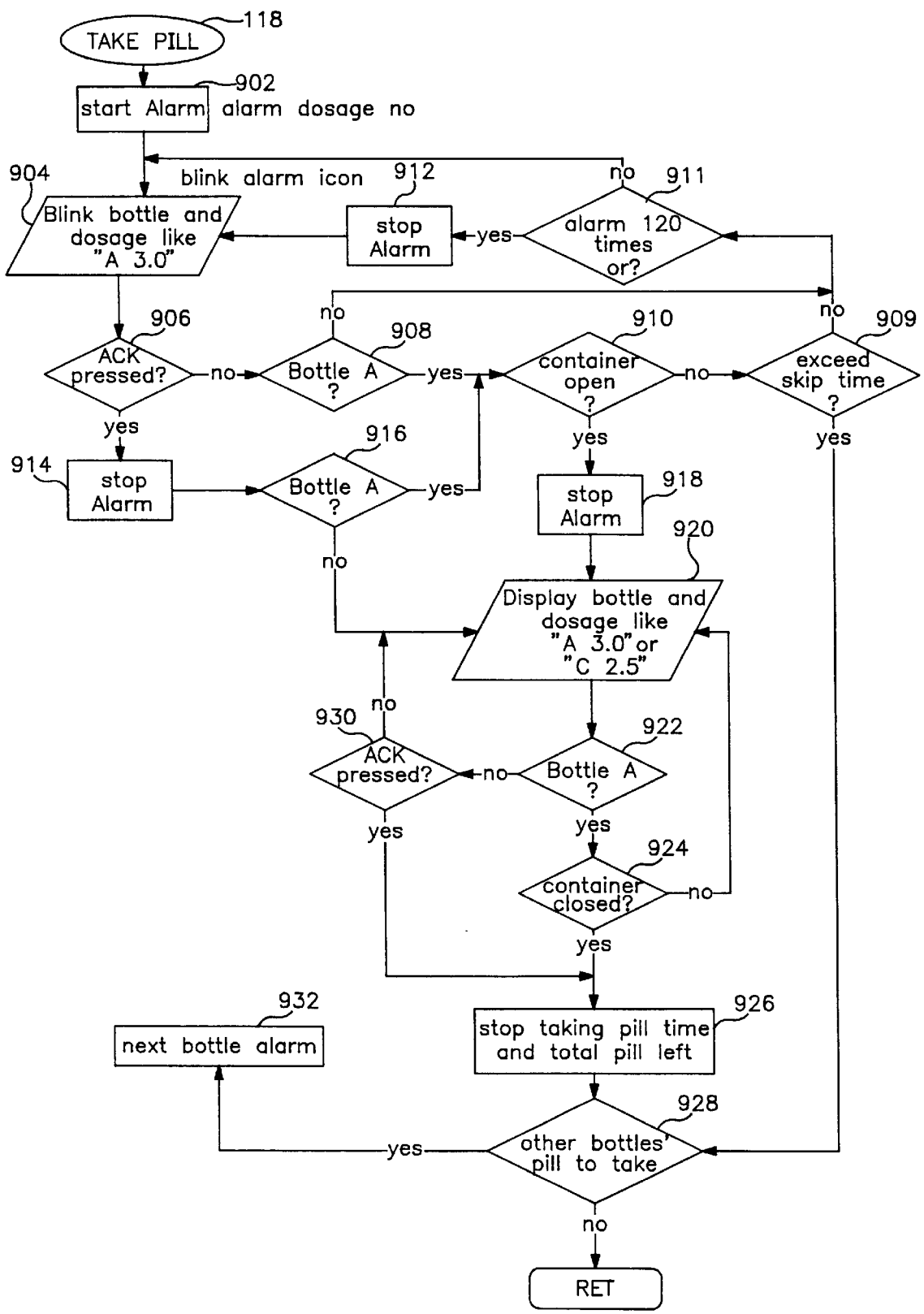

FIG. 15 illustrates what happens when it is actually time to take the medication. When the real time reaches the pre-set medication time, the speaker in the device 10 will set off alarm 902 and a sound beeps the same number of beeps as the dosage to be taken in order to inform a visually impaired patient of the medication time and dosage. The LCD will also blink the bottle number, dosage and alarm icon 904 to indicate it is time to take pills in the bottle or container 24/bottle A indicated on the LCD. Assuming bottle A 908 is selected, opening the container as indicated at 910 even without depressing the ACK key 906 will stop the alarm 918 and blinking 920. If the container is not opened for a period of time that exceeds the skip medication time 909, the device 10 will either return to default real time clock mode or go to next bottle alarm as shown at 928, 932. If the ACK key 906 is not pressed or the container is not opened for bottle A 908 after the alarm has been beeping for 120 times as shown at 911, the beeping will be shut off to save energy. Depressing ACK 906 will acknowledge the warning and stop the alarm 914. For bottle A, the display will still be blinking as shown at 916 until the container is opened as shown at 910 and then the LCD will stop blinking as shown at 920. After the pill(s) in bottle A (container 24) are taken and the container is closed 924, the time the container is closed will be recorded as last medication time and the total pills left will be set as shown at 926. In most circumstances only one bottle (bottle A, for example) is stored within the device 10, with the other bottles labeled but stored external from the device. For bottles other then A, the ACK key has to be depressed a second time 930 in order to record the taking of the medication and reestablishment of the number of pills remaining 926, 928. If there is medication to be taken from other bottles, the alarm will sound 928, 932.

Figure 16:
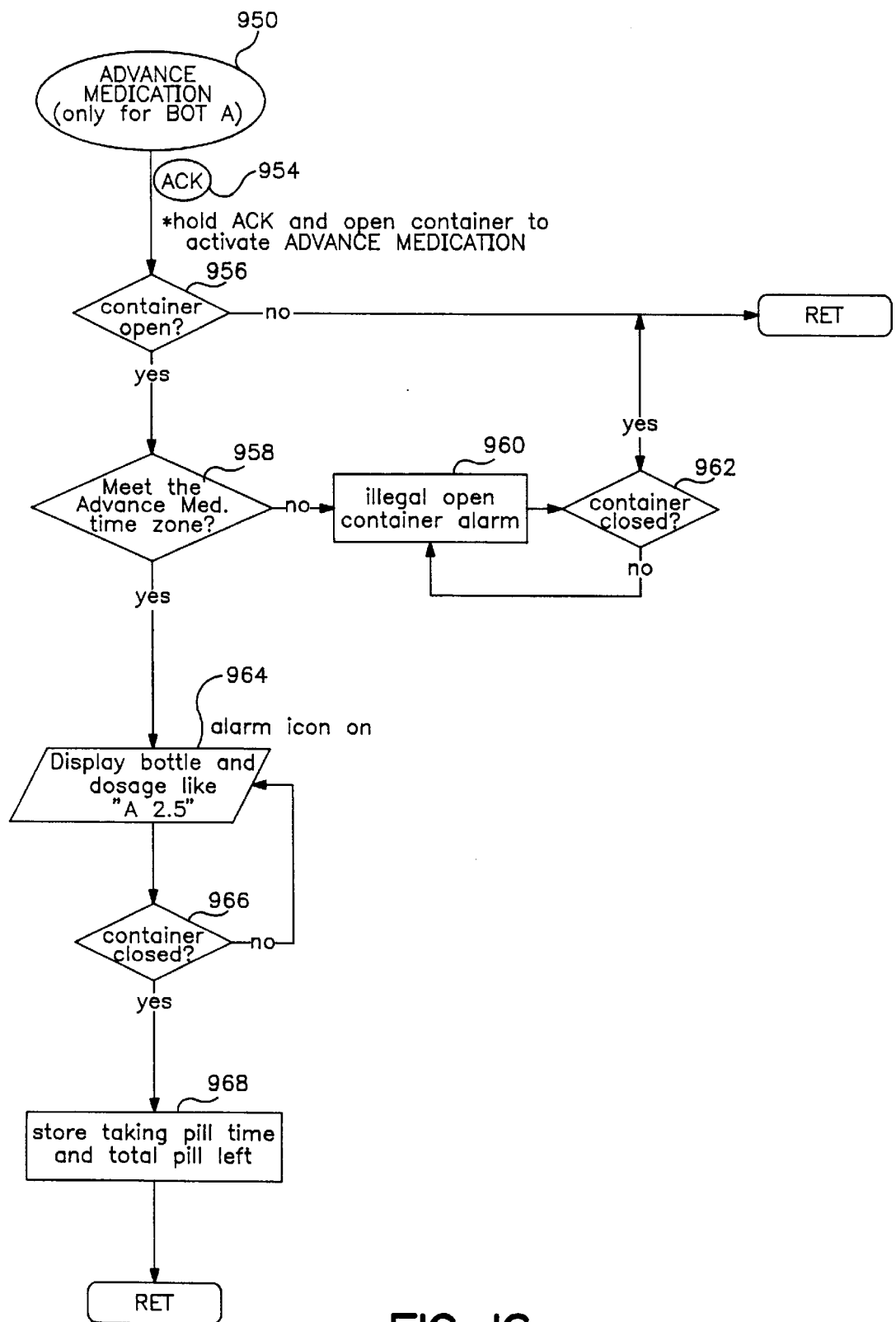

FIG. 16 illustrates the operation of device 10 if medication is taken in advance of the preselected time as shown at 950. In that case, holding the ACK key 954 and opening the container 956 puts the device 10 into the advance medication mode 958. The device 10 will then warn a user as shown at 960 that an improper for action has occurred and the alarm will sound until the container is closed as shown at 962 or, if the time of opening container does not meet the advance medication time zone.

If the opening of the container meets the advance medication time zone, the LCD will display, for example, bottle A (container 24) and the dosage as shown at 964 until the container is closed as shown at 966. The container close time will be recorded as the last medication time and the total pills left as shown in 968 will be recorded.

The present invention has the capability of providing information either in the form of a visual display or an audio signal, whether in the form of pleasant chimes or actual voice directions, related to controlling the dosage or time of taking of medication within or external of the containers 24.

For example, information may be provided with respect to various times of the day in which the medication should be taken. Furthermore, timing and dosage information may be independently altered as well. With respect to the time of day that the medication is to be taken, it is possible to program the device such as to indicate variable dosages at different times of the day whether that dosage be in the form of one, two or even a half a pill. In addition, further indications can be made by the present invention to provide times representative of bedtime or mealtime or predetermined time intervals after meal, or a various day or even a changing dosage requirements.

Audio or visual instructions can be provided by the reminder/dispenser unit 10 of this invention with instructions providing the user with information other than dosages such as whether the medication should be taken with food or without food. Other types of warnings can also be issued and displayed with the present invention such as the avoidance of alcohol with the medication, or pertaining to side effects such as drowsiness or dizziness.

Further information is provided by the reminder/dispenser unit 10 dealing with the number of pills remaining. A memory component of the device informs the user whether or not medication has already been taken. An embodiment of the invention could even incorporate a directory listing important phone numbers which the user needs to reach in the event of a medical emergency.

As stated hereinabove, the reminder/dispenser device 10 of this invention can be programmed either by the user or by a pharmacist or doctor. In certain instances, sealed vials can be utilized in place of the container units so that medication can be dispensed with the assurance that the dosage and time of taking is specifically related to the medication in the sealed vial. This precaution prevents the user from accidentally placing the wrong pills in a container.

The device of the present invention is interactive with respect to inputs from the user, a pharmacist or a doctor and can be programmed from an external computer directly or through a modem. Additionally, the device has an aesthetically pleasing configuration, is extremely light weight and portable. Power is provided to the device by means of a main battery with a back-up battery utilized in conjunction therewith so as to retain all programmed information until the main battery has been replaced. There is also a low-battery indicator which warns of the need for battery replacement.

Although the invention has been described with reference to particular embodiments, it will be understood that this invention is also capable of further and other embodiments within the spirit and scope of the appended claims.

What is claimed is:

1. An interactive, automated medication reminder/dispenser device, said device comprising:

a housing;

means for containing and dispensing therefrom at least one predetermined type of medication, said containing and dispensing means capable of being either mounted within said housing or located external of said housing;

means for establishing a dosage of said at least one predetermined type of medication;

means for establishing at least one preselected time for taking said at least one predetermined type of medication;

means for providing an alarm when said at least one predetermined type of medication is being taken at other than said at least one preselected time, said alarm acting as a warning to a user of the reminder/dispenser device that said medication should not be taken at other than said at least one preselected time, said means for providing said alarm not interacting with the reminder/dispenser device to prevent the user from taking said medication;

means for establishing an advanced medication taking time zone;

means for activating a signal to establish taking of said medication during said advanced medication taking time zone, said signal to establish taking of said medication canceling said alarm;

means for providing a signal indicative of said at least one preselected time to take said at least one medication and further indicative of said dosage of said at least one predetermined type of medication to take at said at least one preselected time;

means for providing an indication of said at least one predetermined type of medication which has been taken, said indication means being activated by the application of a signal thereto, said activation signal being responsive to either the opening of said containing and dispensing means or an independent action;

means for providing information with respect to the amount of said at least one medication remaining after each taking thereof;

said information providing means including means for comparing a series of bits of information in order to provide extremely accurate information with respect to amounts of said at least one predetermined type of medication remaining, wherein said bits of information include information derived from said containing and dispensing means, said means for establishing an advanced medication taking time zone, and means for activating a signal to establish taking of said medication during said advanced medication taking time zone;

means for preselectively varying input to said means for establishing said at least one preselected time for taking said dosage of said at least one predetermined type of medication, and;

said indication means also providing a signal of said varied time and said varied dosage, wherein said varied time can vary from once a day to numerous times a day for each of said at least one predetermined type of medication and said varied dosage can vary for each said varied time and for each of said at least one predetermined type of medication.

2. An interactive, automated medication reminder/dispenser device as defined in claim 1 further comprising means for providing a signal to said signal providing means that medication has been taken at other than at said indicative time and dosage.

3. An interactive, automated medication reminder/dispenser device as defined in claim 1 wherein said containing and dispensing means is mounted within said housing.

4. An interactive, automated medication reminder/dispenser device as defined in claim 1 wherein said means for providing information about the amount of said at least one predetermined type of medication remaining further comprises a mechanism activated by the removal of said medication from said containing and dispensing means.

5. An interactive, automated medication reminder/dispenser device as defined in claim 1 further comprising storing and retrieving means for providing information on said at least one predetermined type of said medication with respect to the time of last taking of, time of next taking of, time between taking of, dosage of, and remaining amount of said at least one preselected type of medication.

6. An interactive, automated medication reminder/dispenser device as defined in claim 1 wherein said varying input means comprises a programmed processor located internal of said housing and a keyboard located on the surface of said housing and through which said device can be programmed and controlled.

7. An interactive, automated medication reminder/dispenser device as defined in claim 1 wherein said varying input means comprises a programmed processor located internal of said housing and a communications port in said housing through which said device can be programmed and controlled.

8. An interactive, automated medication reminder/dispenser device as defined in claim 1 wherein said varying input means comprises a programmed processor located internal of said housing and an optical scanner in said housing through which said device can be programmed and controlled.

9. An interactive, automated medication reminder/dispenser device as defined in claim 1 wherein said varying input means comprises a programmed processor located internal of said housing and a plug-in module capable of interacting with said processor through which said device can be programmed and controlled.

10. An interactive, automated medication reminder/dispenser device as defined in claim 1 wherein said varying input means comprises a programmed processor located internal of said housing and an external computer through which said device can be programmed and controlled.

11. An interactive, automated medication reminder/dispenser device as defined in claim 1 wherein said housing is of a mouse-like configuration.

12. An interactive, automated medication reminder/dispenser device as defined in claim 1 further comprising means for dispensing medication from independently contained sealed vials of medication.

13. An interactive, automated medication reminder/dispenser device as defined in claim 1 wherein said means for providing information with respect to the amount of said at least one medication remaining comprises:

means for detecting opening of said containing and dispensing means; and means for comparing a time of said opening of said containing and dispensing means with said at least one preselected time and with said advanced medication time zone.

14. An interactive, automated medication reminder/dispenser device as defined in claim 1 further comprising means for establishing a skip medication time.

15. An interactive, automated medication reminder/dispenser device as defined in claim 1 wherein said means for providing information with respect to the amount of said at least one medication remaining further comprises:

means for providing an alarm when said containing and dispensing means is opened at other than at said at least one preselected time or said advanced medication taking time zone.

16. An interactive, automated medication/dispenser device as defined in claim 1 wherein said signal indicative of said at least one preselected time to take said at least one medication and further indicative of said dosage of said at least one predetermined type of medication to take at said at least one preselected time is in the form of a visual signal.

17. An interactive, automated medication reminder/dispenser device as defined in claim 1 wherein said means for establishing said dosage of said at least one predetermined type of medication can gradually change the dosage to be taken over a predetermined number of days.

18. An interactive, automated medication reminder/dispenser device as defined in claim 1 further comprising means for establishing a preselected day, days or alternate days for taking said established dosage of said at least one predetermined type of medication.

19. An interactive, automated medication reminder/dispenser device as defined in claim 1 wherein said at least one of said predetermined type of said medication is in the form of pills.

20. An interactive, automated medication reminder/dispenser device as defined in claim 4 wherein said varied dosages can include information with respect to fractional pill requirements or liquid dispensing information.

21. An interactive, automated medication reminder/dispenser device as defined in claim 1 wherein said signal indicative of said at least one preselected time to take said at least one medication and further indicative of said dosage of said at least one predetermined type of medication to take at said at least one preselected time is in the form of an audio signal which can include oral messages with respect to said dosages and time for taking said dosages.

22. An interactive, automated medication reminder/dispenser device as defined in claim 21 wherein said audio signal can include oral messages with respect to warnings with respect to said medication contained within said device.

* * * * *